(12) United States Patent
Gunneson et al.

(10) Patent No.: US 8,357,099 B2
(45) Date of Patent: Jan. 22, 2013

(54) SIGNAL QUALITY DETERMINATION AND SIGNAL CORRECTION SYSTEM AND METHODS

(75) Inventors: Paul B. Gunneson, Cheshire, CT (US); Anthony T. Pierry, Plantsville, CT (US)

(73) Assignee: RIC Investments, LLC, Wilmington, DE (US)

( * ) Notice: Subject to any disclaimer, the term of this patent is extended or adjusted under 35 U.S.C. 154(b) by 1435 days.

(21) Appl. No.: 11/957,995

(22) Filed: Dec. 17, 2007

(65) Prior Publication Data

US 2008/0161710 A1    Jul. 3, 2008

Related U.S. Application Data

(60) Provisional application No. 60/876,798, filed on Dec. 21, 2006.

(51) Int. Cl.
    *A61B 5/08*    (2006.01)
(52) U.S. Cl. ...................................... 600/532
(58) Field of Classification Search ........................ None
    See application file for complete search history.

(56) References Cited

U.S. PATENT DOCUMENTS

| | | | |
|---|---|---|---|
| 4,440,177 A | 4/1984 | Anderson et al. | |
| 4,856,531 A | 8/1989 | Merilainen | |
| 5,190,729 A | 3/1993 | Hauenstein et al. | |
| 5,727,545 A | 3/1998 | Psaros | |
| 5,789,660 A | 8/1998 | Kofoed et al. | |
| 6,312,389 B1 | 11/2001 | Kofoed et al. | |
| 6,325,978 B1 | 12/2001 | Labuda et al. | |
| 6,616,896 B2 | 9/2003 | Labuda et al. | |
| 6,632,402 B2 | 10/2003 | Blazewicz et al. | |
| 6,815,211 B1 | 11/2004 | Blazewicz et al. | |
| 6,888,101 B2 | 5/2005 | Davis | |
| 7,023,915 B2 | 4/2006 | Pian et al. | |
| 2002/0029003 A1 | 3/2002 | Mace et al. | |
| 2004/0254491 A1 | 12/2004 | Ricciardelli | |
| 2005/0145796 A1 | 7/2005 | Davis | |
| 2006/0014078 A1 | 1/2006 | Swoyer et al. | |

OTHER PUBLICATIONS

U.S. Appl. No. 11/948,080, filed Nov. 30, 2007, Orr et al.

*Primary Examiner* — Shanon A Foley

(57) ABSTRACT

A mainstream gas monitoring system and method that includes using a mainstream airway adapter and a gas sensing assembly associated with the airway adapter to measure an analyte of a gas flow through the adapter. A gas sensing portion outputs a signal indicative of the analyte in a gas flow in the mainstream airway adapter. A processing portion receives the signal from the gas sensing portion and determines an amount of the analyte in the gas flow based on the signal from the gas sensing portion. The processing portion determines whether the oxygen measurements are of sufficient quality for their intended use, such as for measuring oxygen consumption or metabolic estimations. Quality measurements may be used to improve accuracy of derived metabolic estimations. Methods are provided by which carbon dioxide measurements can be processed and substituted for direct oxygen measurement for all or part of a respiratory cycle.

15 Claims, 11 Drawing Sheets

SIGNAL QUALITY DETERMINATION AND SIGNAL CORRECTION SYSTEM AND METHODS

CROSS-REFERENCE TO RELATED APPLICATIONS

This application claims priority under 35 U.S.C. §119(e) from provisional U.S. patent application No. 60/876,798 filed Dec. 21, 2006 the contents of which are incorporated herein by reference.

BACKGROUND OF THE INVENTION

1. Field of the Invention

The present invention pertains to a system and method for monitoring a metabolic parameter of a user.

2. Description of the Related Art

It is well known to monitor the oxygen consumption or oxygen uptake of an individual for purposes of monitoring the physiologic condition of that person. The phrases "oxygen uptake" and "oxygen consumption" are used synonymously, and are both represented by the expression "$V_{O_2}$" or, for simplicity "$VO_2$". Oxygen consumption is a measure of the amount of oxygen that the body uses in a given period of time, such as one minute. It is typically expressed as milliliters of oxygen used per kilogram of body weight per minute (ml/kg/min). Measuring the rate of oxygen consumption is valuable, for example, in anesthesia and intensive care situations because it provides an indication of the sufficiency of a patient's cardiac and pulmonary function. $VO_2$ can also be used to monitor the fitness of an individual or athlete.

$VO_2$ is conventionally calculated as the difference between the volume of oxygen inspired and the volume of oxygen expired. The standard or direct calculation of $VO_2$ is given by the following equation:

$$VO_2 = Vi \ast Fi_{O2} - Ve \ast \overline{Fe}_{O2}, \quad (1)$$

where: "$VO_2$" is oxygen consumption, "Vi" is inspired volume, "$Fi_{O2}$" is the inspired oxygen concentration, "Ve" is the expired volume, and "$\overline{Fe}_{O2}$" is the mixed expired oxygen concentration.

An alternative method of calculating $VO_2$ uses only the expired breath volume, Ve. In this scenario, the inspired breath volume Vi is calculated (rather than measured) based on the assumption that the nitrogen volume is the same for both inspired and expired gas, which is usually true because nitrogen is not consumed or produced by the body. This is referred to as the nitrogen balance. The calculation of Vi, rather than measuring it, also assumes that the effect of temperature and humidity are the same for both inspired and expired gas volumes.

This modification of equation (1), which uses a calculation of Vi based on the nitrogen balance noted above, is known as the Haldane transform. According to this technique, Vi is calculated as follows:

$$Vi = Ve \ast \overline{Fe}_{N2} / Fi_{N2}, \quad (2)$$

where "$\overline{Fe}_{N2}$" is the concentration of expired nitrogen, and "$Fi_{N2}$" is the concentration of inspired nitrogen. Based on this, the Haldane transform becomes:

$$Vi = Ve \ast (1 - \overline{Fe}_{CO2} - \overline{Fe}_{O2}) / (1 - Fi_{CO2} - Fi_{O2}), \quad (3)$$

and the oxygen consumption calculation becomes:

$$VO_2 = Ve \ast [Fi_{O2} \ast ((1 - \overline{Fe}_{CO2} - \overline{Fe}_{O2})/(1 - Fi_{CO2} - Fi_{O2})) - \overline{Fe}_{O2}], \quad (4)$$

where "$\overline{Fe}_{CO2}$" is the expired carbon dioxide concentration, and $Fi_{CO2}$ is the inspired carbon dioxide concentration.

Calculating $VO_2$ using the Haldane transform has the advantage that the effects of errors in volume measurements that are not "common mode" are eliminated, because only the expired volume measurement is used. Common mode errors are errors that effect both the Vi and Ve measurements, such as a calibration error in a flow sensor. Assuming, of course, the same sensor is used to measure Ve and Vi.

Conventional $CO_2$ sensor technology is generally capable of very fast and accurate measurement of airway $CO_2$ and can be sufficiently robust to track changes in respiratory $CO_2$ over long periods of time. It is desirable to measure respiratory oxygen with similar speed and accuracy, so that one or more parameters such as oxygen consumption, energy expenditure, respiratory quotient, or related metabolic measurements can be accurately assessed. This can be used for various applications such as respiratory spirometry, for example.

Although mainstream oxygen sensing technology that is potentially fast and accurate enough to use for such applications is becoming available, speed and robustness may be inferior to available $CO_2$ sensing technology. Estimations of oxygen consumption or metabolic parameters derived from measurements of respiratory gasses can only be accurate if all the gas measurements are sufficiently accurate. A method of determining if airway conditions interfere with the measurement of oxygen is also needed to ensure that a corrupted waveform is not used to calculate oxygen consumption or other metabolic parameters. Given that fast, accurate, and robust oxygen measurement may be the limiting factor in attaining respiratory measurements for oxygen consumption or metabolic assessment, methods to help identify corrupted oxygen waveforms and to correct such waveforms are desired.

It should also be appreciated, however, that the present invention can be applied to sensing of other gasses, and is not limited to measurements of oxygen or carbon dioxide.

SUMMARY OF THE INVENTION

Accordingly, it is an object of the present invention to provide a gas monitoring system that overcomes the shortcomings of conventional gas monitoring system. Certain embodiments of the present invention take advantage of known physical properties of respiratory gas exchange that can be applied when a robust, fast and accurate $CO_2$ sensor is used in conjunction with a less robust oxygen sensor. In certain embodiments, methods are provided that use the carbon dioxide measurements to determine whether the oxygen measurements are of sufficient quality to use for oxygen consumption or other metabolic estimations. Such quality determinations can be used to improve accuracy of derived calculations, such as oxygen consumption and metabolic estimations, that could otherwise be limited when the quality of the measurements from an oxygen sensor is inferior to the quality of measurements in a carbon dioxide sensor. In certain embodiments, methods of using carbon dioxide measurements to enhance oxygen measurements are provided.

In accordance with one of embodiment of the invention, there is provided a system for measuring respiratory gases that includes a first gas sensor constructed and arranged to measure an amount of a first gas, a second gas sensor constructed and arranged to measure an amount of a second gas, and a processor operatively connected with the first gas sensor and the second gas sensor. The processor receives a first signal from the first gas sensor and a second signal from the second gas sensor. The processor adjusts the measured amount of the first gas based upon the measured amount of the second gas.

In accordance with another embodiment of the invention, there is provided a system for measuring respiratory gases that includes a first gas sensor that measures an amount of inspired and expired oxygen, a second gas sensor that measures at least an amount of expired $CO_2$, and a processor operatively connected with the first gas sensor and the second gas sensor. The processor receives signals from the first gas sensor and from the second gas sensor and adjusts the measured amount of oxygen based upon the measured amount of $CO_2$.

In accordance with another embodiment of the invention, there is provided a method for measuring respiratory gases that includes the steps of measuring an amount of a first gas, measuring an amount of a second gas, determining if the measured amount of the first gas requires adjustment, and adjusting the measured amount of the first gas based upon the measured amount of the second gas if the first gas requires adjustment.

In accordance with another embodiment of the invention, there is provided a system for measuring respiratory gases that includes a means for measuring an amount of a first gas, means for measuring an amount of a second gas, and means for adjusting a measured amount of the first gas based upon a measured amount of the second gas.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
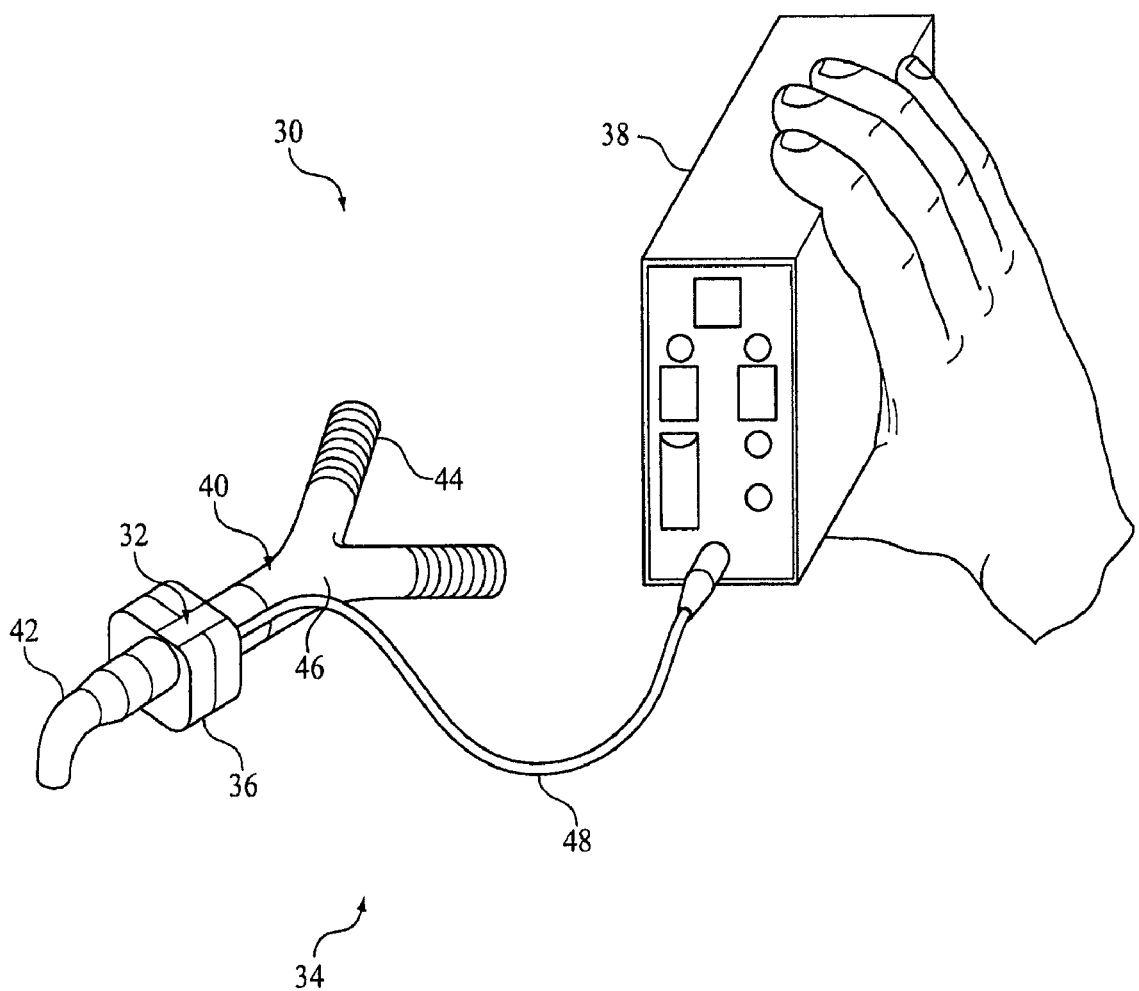
FIG. 1 is a perspective view of a first embodiment of a gas sensing system according to the principles of the present invention.

FIG. 1 schematically illustrates an exemplary embodiment of a mainstream gas monitoring system 30 according to the principles of the present invention. Gas monitoring system 30 includes an airway adapter 32 for use in a respiratory circuit 40, and a gas sensing assembly, generally indicated at 34. The respiratory circuit 40 is used to communicate a flow of gas to a patient. For example, a first end 42 of respiratory circuit 40 is connected with a patient interface appliance configured to communicate with an airway of a patient. Examples of patient interface appliances that are suitable for use with respiratory circuit 40 include, but are not limited to: an endrotracheal tube, a nasal cannula, a tracheotomy tube, a mask, or any other device or apparatus that communicates a flow of gas with an airway of a user.

A second end 44 of respiratory circuit 40 is configured to communicate with a gas source. For instance, the gas source may include ambient atmosphere, a supply of pressurized gas, a pressure support device, a ventilator, or other sources of gas. In the illustrated embodiment, the second end 44 includes a Y-connector 46, which is typically found in a ventilator circuit, is shown connected to the second end of the airway adapter. One leg of the Y-connector corresponds to the inspiratory limb, which delivers gas from a ventilator (not shown) to the patient, and the other leg of the Y-connector corresponds to the expiratory limb, which delivers gas from the patient. Typically, the gas is delivered by the expiratory limb back to the ventilator, which is the gas source in this embodiment. In a single limb system (not shown), the second end comprises a single conduit that communicates a flow of gas between the patient and the gas source, which is often a pressure support system, such as a CPAP, bi-level, or auto-titrating pressure support device.

Figure 2:
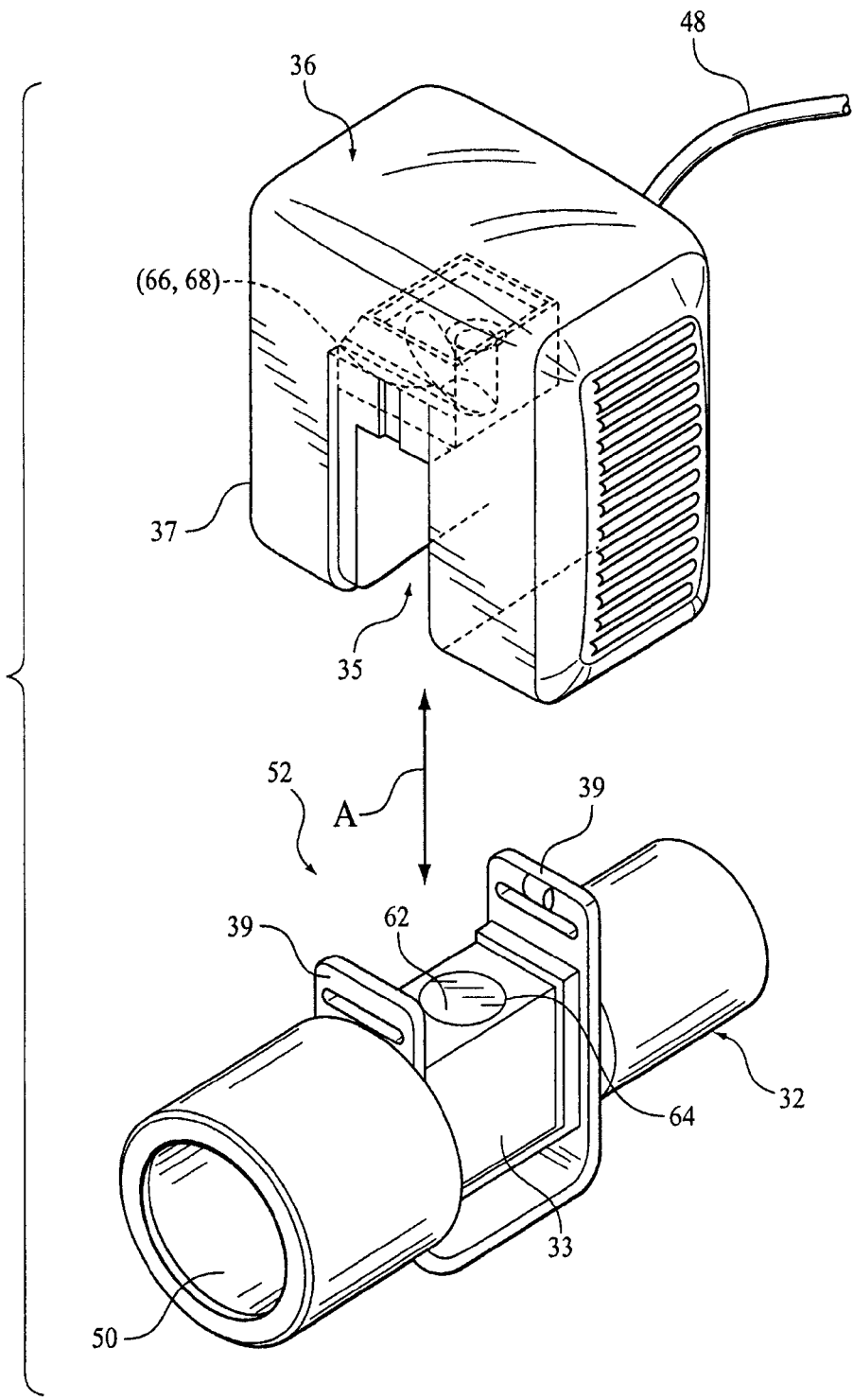
FIG. 2 is a perspective view of an airway adapter and gas sensor in the gas sensing system of FIG. 1.
Figure 3:
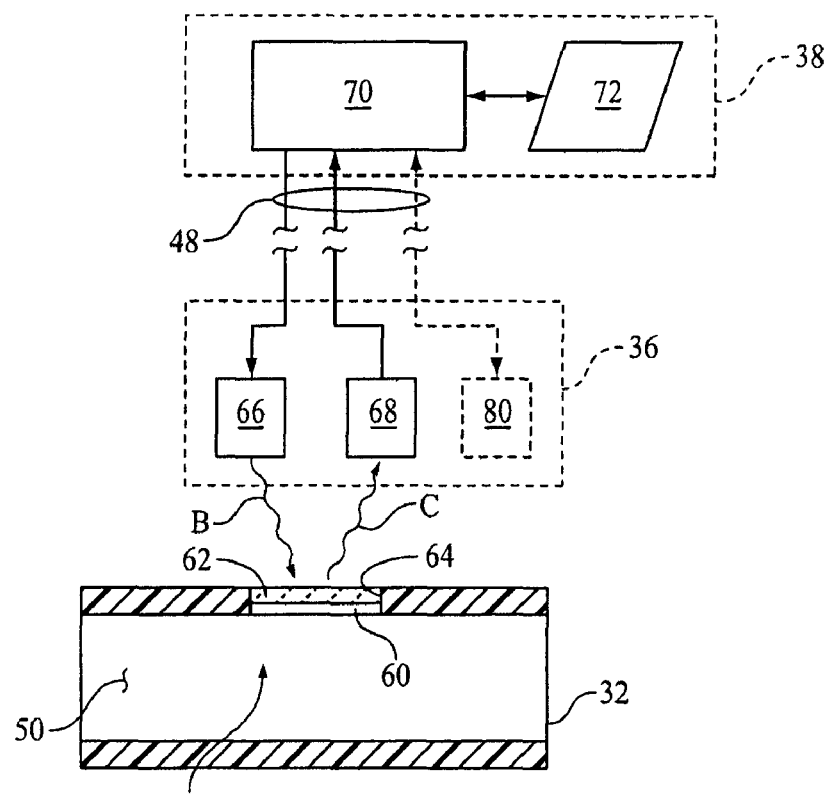
FIG. 3 is a schematic view of the components of the gas sensing system of FIG. 1.

As perhaps best shown in FIGS. 2 and 3, airway adapter 32 provides a flow path 50 in-line with respiratory circuit 40 through which gas passes to and from the patient. The airway adapter 32 also provides a gas monitoring portion or sample site, generally indicated at 52, at which the constituents of the gas passing through the airway adapter are monitored or measured. Examples of airway adapter suitable for use in the present invention are described in U.S. Pat. Nos. 5,789,660 ("the '660 patent") and 6,312,389 ("the '389 patent"), and in U.S. patent application Ser. No. 09/841,451 ("the '451 application," publication no. 2002/0029003), the contents of each of which are incorporated herein by reference in their entirety.

In the embodiment illustrated in FIGS. 1-3, gas sensing assembly 34 includes a gas sensing portion 36 and a processing portion 38. In this illustrated exemplary embodiment, gas sensing portion 36 is removably coupled to airway adapter 32, as indicated by arrow A, and includes the components that are used to detect the gas constituent or constituents, also referred to as analyte, being monitored. It should be appreciated that a variety of mechanisms may be implemented to removably couple gas sensing portion 36 to airway adapter 32. In an exemplary embodiment shown in FIG. 2, a seating area 33 is provided on an outer surface of airway adapter 32 that is adapted to securely receive a housing 37 of gas sensor portion 36. Housing 37 is generally "U" shaped to fit onto seating area 33 with a channel 35 that receives the generally matching shape of the seating area of the airway adapter. Flanges 39 can be provided on the airway adapter to align and attach the housing to the airway adapter. U.S. Pat. Nos. 6,616,896 ("the '896 patent") and 6,632,402 ("the '402 patent"), the contents of each of which are incorporated hereby by reference, describe techniques for coupling gas sensing portion 36 to airway adapter 32. The present invention also contemplates permanently connecting gas sensing portion 36 to airway adapter 32 so that the functionality of each component is effectively combined into a common element.

A communication link 48 allows data, power, and any other signals, commands, etc. to be communicated between gas sensing portion 36 and processing portion 38. Although a hard wired communication link 48 is shown in FIGS. 1-3, it is to be understood that the present invention contemplates that the communication link can be a wireless link, using any form of wireless communication or communication protocol. Of course, if a wireless link is provided, a power supply, such as a battery, must be included in gas sensing portion 36 or power must be provided in some other manner to the gas sensing portion.

Gas sensing assembly 34 detects the concentration of one or more gases (analytes) in the flow of gas through the sample cell. In an exemplary embodiment illustrated in FIGS. 1-3, gas sensing assembly 34 is configured to employ luminescence quenching techniques to measure the partial pressure or amount of oxygen or other gases that flow through airway adapter 32. This oxygen measurement is used, for example, to determine the value for $Fi_{O2}$ and $\bar{Fe}_{O2}$.

Luminescence quenching is a technique that has been used to measure oxygen concentrations in gases. In using luminescence quenching to measure oxygen concentrations, a luminescable material 60 (see FIG. 3) is excited to luminescence by delivering an excitation energy, as indicated by arrow B, to the luminescable material. Upon being excited to luminescence, the luminescable material will emit energy, as indicated by arrow C. However, when the luminescing material is exposed to a gas mixture including oxygen, the luminescence is quenched, depending upon the amount (i.e., concentration or fraction) of oxygen to which the luminescable material is exposed, or the amount of oxygen in the gas mixture. Accordingly, the rate of decrease in the amount of luminescence, or quenching of luminescence, of the luminescable material (i.e., the amount of light emitted by the luminescable material) corresponds to the amount of oxygen in the gas mixture. Thus, the energy emitted by the luminescable material can be used to determine the concentration of the gas passing through the airway adapter. U.S. Pat. Nos. 6,325,978; 6,632, 402; 6,616,896; and 6,815,211, the contents of each of which are incorporated herein by reference, all disclose an example of an oxygen sensor that uses luminescence quenching to determine the concentration of a gas, such as oxygen, in the gas flowing through a sample cell.

As shown in FIGS. 1-3, a quantity of luminescable material 60 is situated such that it is exposed to the gas flowing in flow path 50 through airway adapter 32. The present invention also contemplates providing a combination of luminescable materials in communication with the gas flowing through the airway adapter. Porphyrins are an example of a material that may be used as luminescable material 60. Porphyrins are stable organic ring structures that often include a metal atom. When the metal atom is platinum or palladium, the phosphorescence decay time ranges from about 10 μs to about 1,000 μs. Porphyrins are also sensitive to molecular oxygen. When porphyrins are used as luminescable material 60, it is preferred that the porphyrins retain substantially all of their photo-excitability with repeated use. Stated another way, it is preferred that the porphyrins be "photostable". Fluorescent porphyrins, such as meso-tetraphenyl porphines, are particularly photostable. The various types of porphyrins that may be used as luminescable material 30 to facilitate oxygen detection include, without limitation, platinum meso-tetra(pentafluoro)phenyl porphine, platinum meso-tetraphenyl porphine, palladium meso-tetra(pentafluoro)phenyl porphine, and palladium meso-tetraphenyl porphine. Of course, other types of luminescable materials that are known to be quenched upon being exposed to oxygen, carbon dioxide, or another analyzed substance (e.g., gas, liquid, or vapor) may also be used in airway adapters incorporating teachings of the present invention.

In the illustrated embodiment, luminescable material 60 is provided on airway adapter 32, and a window 62 is provided in an opening 64 in the body of the airway adapter to allow excitation energy B to be transmitted to the luminescable material. Window 62 preferably has a high transmittance for wavelengths of excitation radiation, which excite luminescable material 60, as well as for wavelengths of radiation C emitted from luminescable material. For example, window 62 may be formed of sapphire, one or more polymers (e.g., polyethylene, etc.), a glass, and/or other substantially transparent materials.

In an exemplary embodiment, luminescable material 60 is carried by a membrane or matrix, which is disposed on or comprises an integral part of a surface or wall of the airway adapter defining gas flow path 50. The present invention also contemplates that the luminescable material and associated components, such as a membrane, need not be directly coupled to the airway adapter, but can be selectively coupled so that the luminescable material can be replaced without having to remove or replace the entire airway adapter.

An emitter 66 is provided in gas sensing portion 36 to emit excitation energy B to luminescable material 60. In an exemplary embodiment of the present invention, the energy emitted by emitter 66 includes electromagnetic radiation with a wavelength that causes luminescable medium 60 to luminensce. Emitter 66 may include one or more Organic Light Emitting Diodes ("OLEDs"), lasers (e.g., diode lasers or other laser sources), Light Emitting Diodes ("LEDs"), Hot Cathode Fluorescent Lamps ("HCFLs"), Cold Cathode Fluorescent Lamps ("CCFLs"), incandescent lamps, halogen bulbs, received ambient light, and/or other electromagnetic radiation sources.

In one exemplary implementation, emitter 66 includes one or more green and/or blue LEDs. These LEDs typically have high intensity in the luminescable composition absorption region of luminescable medium 60 and output smaller amounts of radiation at other wavelengths (e.g., red and/or infrared). This minimizes stray interfering light and photo-degradation of the sensor. While, the present invention is by no means limited to the use of LEDs, other advantages of implementing LEDs as emitter 30 include their light weight, compactness, low power consumption, low voltage requirements, low heat production, reliability, ruggedness, relatively low cost, and stability. Also they can be switched on and off very quickly, reliably, and reproducibly.

A detector 68 is provided in gas sensing portion 36 to detect radiation C. Detector 68 is positioned within gas sensing portion 36 such that when gas sensing portion 3 and airway adapter 32 are coupled, detector 68 receives at least a portion of luminesced electromagnetic radiation C from luminescable medium 60. Based on the received radiation, detector 60 generates one or more output signals related to one or more properties of the received radiation. For example, the one or more output signals may be related to an amount of the radiation, an intensity of the radiation, a modulation of the radiation, and/or other properties of the radiation. In one embodiment, detector 68 includes a PIN diode. In other embodiments, other photosensitive devices are employed as detector 68. For instance, detector 68 may take the form of a diode array, a CCD chip, a CMOS chip, a photo-multiplier tube and/or other photosensitive devices.

Luminescable medium 60, in response to radiation B from emitter 66, emits electromagnetic radiation C in a substantially omni-directional manner at a wavelength different from that of the electromagnetic radiation provided by the emitter. The intensity and/or persistence of this luminesced electromagnetic radiation rises and falls according to the relative amounts of one or more analytes, such as oxygen, included in the body of gas within gas flow path 50. In one embodiment, oxygen causes a modification of the intensity and/or persistence of luminescent radiation B by quenching the luminescence reaction. As the concentration of oxygen increases, the modification of the intensity and/or persistence of luminescent radiation B decreases. In one embodiment, luminescable medium 60 is formed as a luminescent film. For example, both of the incorporated '896 and '402 patents disclose films that may be employed as luminescable medium 60.

Based on the output signal from gas sensing portion 36, processing portion 38 determines information related to one or more properties of one or more analytes or constituents included in the gas disposed within flow path 50. In the illustrated exemplary embodiment, processing portion 38 includes a processor 70 that controls emitter 66 and receives the signal from detector 68. Processor 70 uses the signal from detector 68 to determine the oxygen concentration as discussed in detail below. Although not shown, processor 70 and/or processing portion 38 may include other components typically used to monitor gas constituents, such as memory (RAM, ROM).

As shown in FIG. 3, the present invention contemplates that processing portion 38 includes an input/output device 72 or devices for providing an output of processor 70 in a human perceivable format. In an exemplary embodiment, input/output device 72 is a monitor or display that visually indicates the oxygen concentration to the user. The present invention also contemplates that input/output device 72 includes communication elements, such as terminals, transceivers, modems, etc. for communicating an output of processor 70 to a remote location. This can be done wirelessly, via a hardwire communication system, or using any combination thereof.

Figure 4:
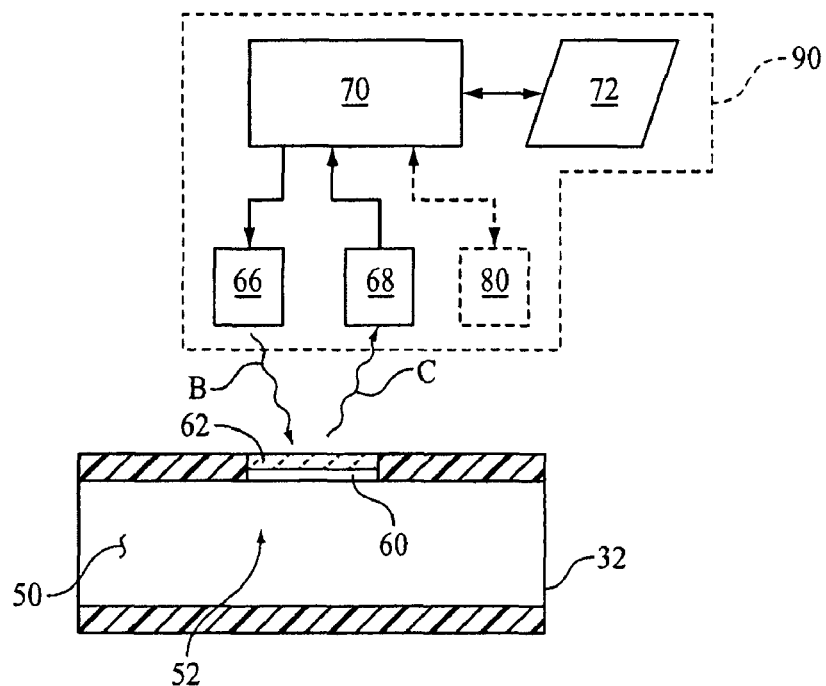
FIG. 4 is schematic view of the components of a second embodiment of a gas sensing system according to the principles of the present invention.
Figure 5:
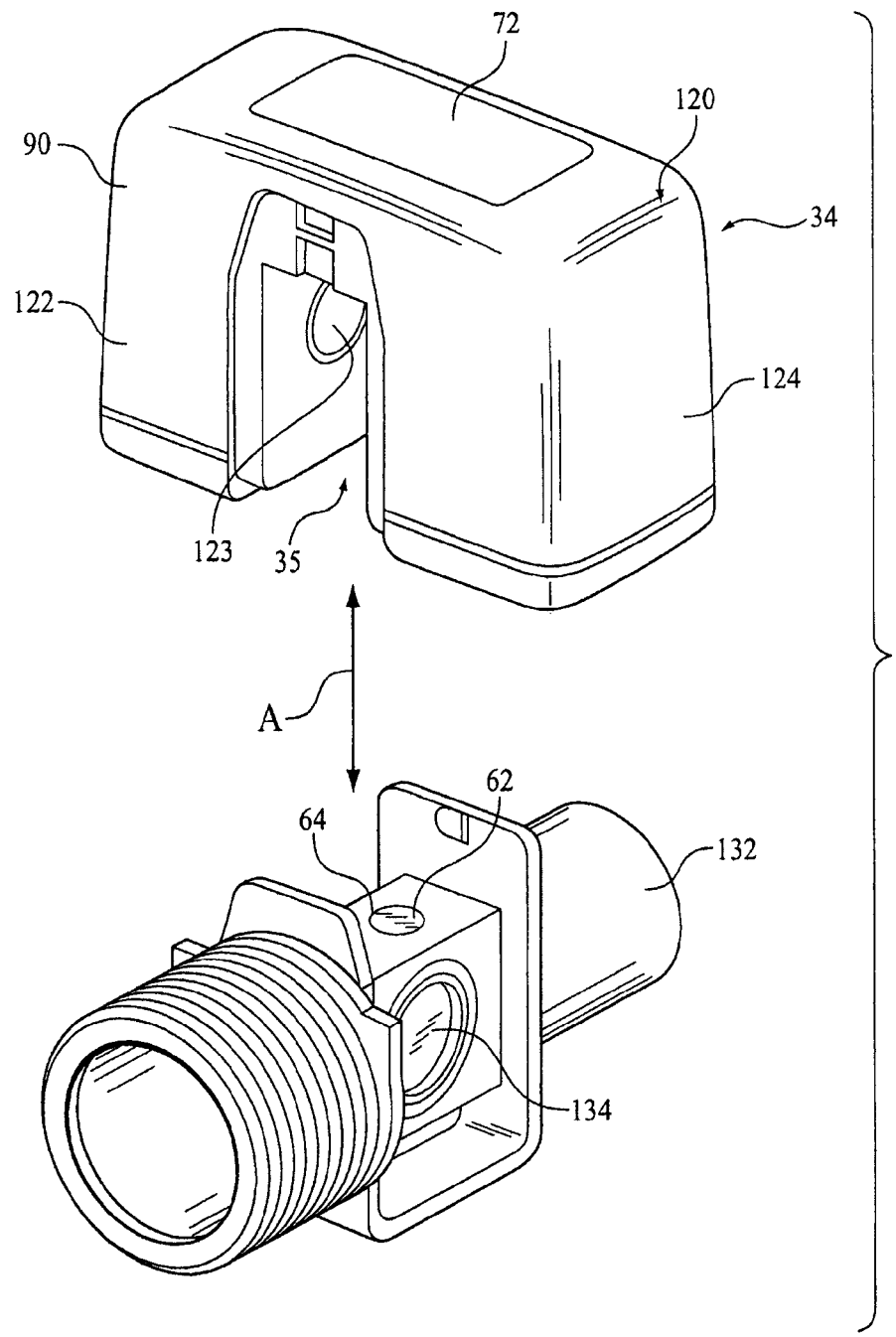
FIG. 5 is a perspective view of an airway adapter and gas sensor according to a third embodiment of the present invention.

In the embodiments of FIGS. 1-3, gas sensing portion 36 and processing portion 38 are separate structures that contain their respective components. The present invention also contemplates that these two portions can be combined into a common gas sensing/processing portion 90, as shown schematically in FIG. 4 and in FIG. 5. That is, all of the components necessary to detect, monitor, determine, display, and communicate information pertaining to the gas concentration, such as $VO_2$ can be provided in the sensor head 90 that attaches to airway adapter 32. An example of a sensor head 90 having such functionality is shown in FIG. 5 and is disclosed, for example, in U.S. patent application Ser. No. 11/368,832 (publication no. US-2006-014078-A1), the contents of which are incorporated herein by reference.

The present invention contemplates that additional components can be used in gas sensing portion 36. For example, one or more filter elements can be positioned within the gas sensing portions, e.g., between luminescable medium 60 and detector 68. Such filter elements are typically designed to prevent electromagnetic radiation that is not emitted by the luminescable medium from becoming incident on the detector. For instance, in one embodiment, the filter elements are wavelength specific and permit luminescence radiation C to pass therethrough to become incident on detector 68 while substantially blocking radiation with other wavelengths.

Other components that can be used in gas sensing portion 36 include a reference detector and a beam splitting element that directs a portion of the radiation propagating toward detector 68 onto the reference detector. One or more output signals generated by the reference detector may be provided to processor 70 and used as a reference to account, and compensate, for system noise (e.g., intensity fluctuations in emitter 66, etc.) in the signals generated by detector 68.

In some implementations, gas sensing portion 36 may include one or more optical elements (not shown) to guide, focus, and/or otherwise process radiation emitted by emitter 66 or provided to detector 68. For example, one or more lenses may collimate the radiation in a selected direction. As more particular examples, both of the incorporated '896 and '402 patents disclose the use of optical elements that process radiation emitted by an emitter similar to emitter 66.

The present invention further contemplates using a thermal capacitor to maintain luminescable medium 60 at a substantially constant operating temperature to reduce or eliminate inaccuracies in gas measurement system 30 attributable to variations in the temperature of the luminescable medium. Thus, the thermal capacitor is any device that accomplishes this function, such as a heater controlled in a feedback fashion based on an output of a temperature sensor, a heat sink, or the like. Examples of suitable thermal capacitors in the form of heating elements are disclosed in U.S. Pat. No. 6,888,101 and in U.S. patent application Ser. No. 11/069,114 (publication no. US-2005-0145796-A1), the contents of each of which are incorporated hereby by reference.

In the embodiment illustrated in FIGS. 1-4, a single window 62 is provided on the airway adapter. The present invention also contemplates providing two windows similar to window 62 in the airway adapter. As is shown and described in the '402 patent, the two windows may be disposed in airway adapter 32 opposite from each other to enable electromagnetic radiation to pass through the adapter. In this embodiment, a detector 32 may be positioned on an opposite side of the airway adapter from emitter 66 when sensor.

The present invention also contemplates that airway adapter 32 can include other one or more additional gas measuring and/or sensing components. These other sensing components are schematically illustrated as 80 in FIG. 3. Examples of such sensors include temperature, light, sound, humidity, pressure, flow, and gas concentration sensors. Such sensors can be used to monitor the flow of gas, gas sensing portion 36 or both. For example, a temperature sensor can be provided in housing 37 to detect overheating in the housing. A temperature sensor can also be provided to detect the temperature of the gas flowing in the airway adapter.

FIG. 5 illustrates a gas monitoring system that includes both a carbon dioxide ($CO_2$) concentration detecting capability and an oxygen ($O_2$) concentration detecting capability. The oxygen concentration detecting system corresponds to the luminescence quenching technique discussed above and includes a luminescable material disposed on window 62 of an airway adapter 132. The $CO_2$ monitoring system is an absorption type gas (analyte) detection system in which energy is transmitted from an emitter (not shown) disposed on one leg of a housing 120 (such as leg 122). A window 123 is shown on an interior surface of leg 122 from which the energy exits housing 120. The energy is provided to a first window (not shown) defined in the airway adapter. It passes through a gas sample (the gas flowing through gas flow path 50), and out a second window 134 also defined in the airway adapter generally opposite the first window. The energy exiting the sample site via second window 134 is measured by a detector (not shown) provided in second leg 124.

As known in the art, the signal from the detector is used to determine the gas (analyte) concentration. For example, it is know to use the output of this type of absorption system to detect the amount of $CO_2$ in the gas passing through the airway adapter, which is used to determine the amount of expired $CO_2$ ($\overline{Fe}_{CO2}$) and the amount of inspired $CO_2$ ($Fi_{CO2}$). The signal from the detector can be processed by a processor provided in housing 37 or sent wirelessly or via a hardwire 48 to a separate processing portion. In this illustrated embodiment, the processing portion is incorporated into housing 120 and the resultant analyte measurement is shown on display 72.

In a similar fashion, the present invention further contemplates that the airway adapter can be configured to include a flow sensing system to measure the flow or flow rate of gas passing through the airway adapter. The flow rate is used to determine the amount of analyte passing through the airway adapter over a given period of time or during a respiratory cycle or phase thereof.

One type of flow sensing system suitable for use in this embodiment of the present invention is a pneumotach type of flow sensor. Such a flow sensor includes a flow element (not shown) that is disposed in the gas flow path so as to create a pressure drop in the flow of gas along the gas flow path. The pressure drop created by the flow element is measured and used to determine the flow rate.

Figure 6:
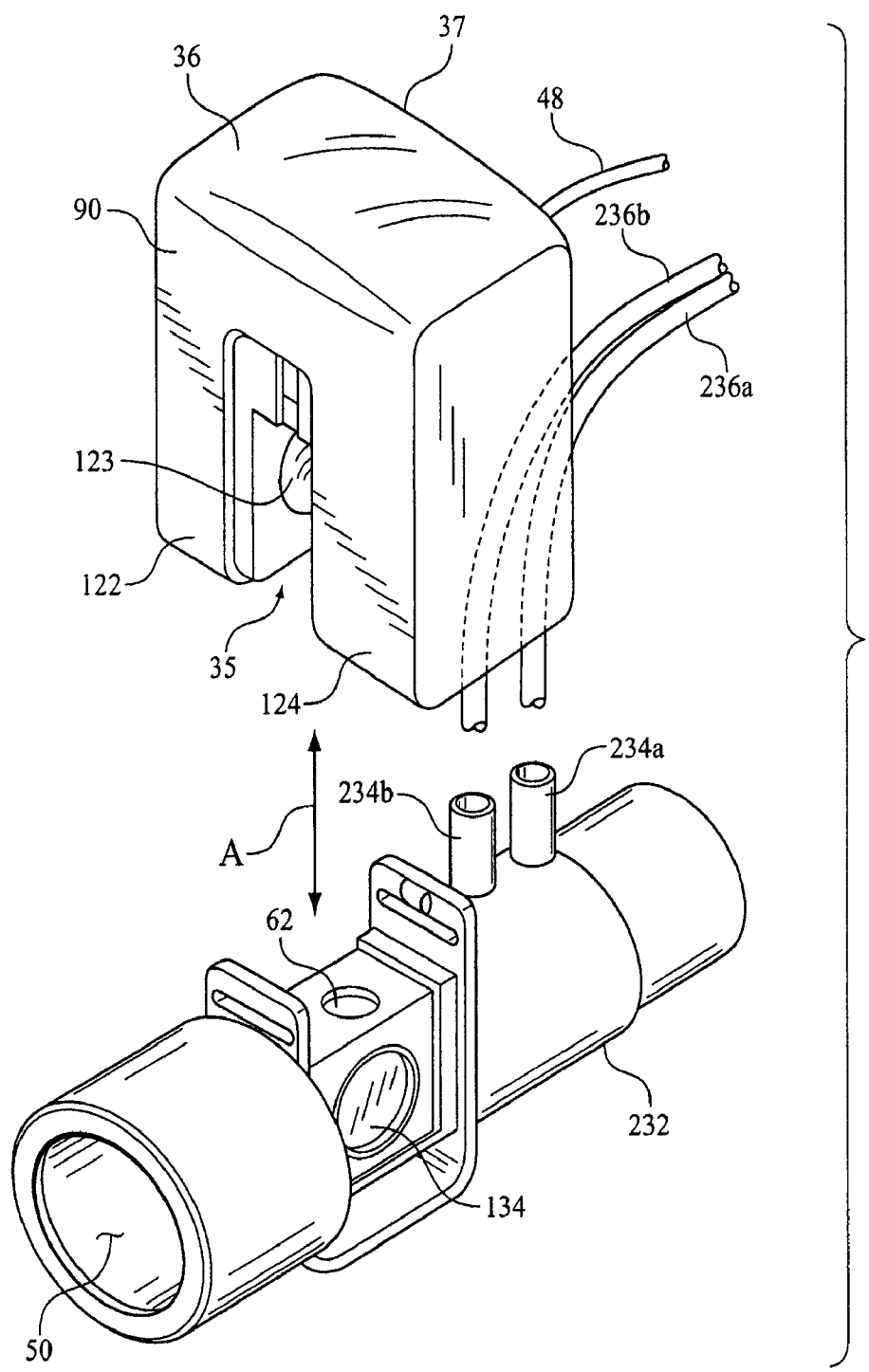
FIG. 6 is a perspective view of an airway adapter and gas sensor according to a still further embodiment of the present invention.

FIG. 6 illustrates an airway adapter 232 having such a flow sensing capability. It should be noted that airway adapter also has an $O_2$ and $CO_2$ sensing capability using the techniques discussed above. Airway adapter 232 includes a pair of ports 234a and 234b that are provided on each side of the flow element contained within the airway adapter. These pressure sensing elements allow the pressure drop across the flow element to be measured so that the flow of gas through the airway adapter can be measured quantitatively. For example, a pair of tubes or pneumatic hoses 236a and 236b can be coupled to ports 234a and 234b to and to a pressure sensor or sensors in processing portion 38 (see FIG. 1). The pressure sensors measure the pressure drop and this output is used to determine the flow through the airway adapter.

In the embodiment illustrated in FIG. 6, the additional flow sensing function is not contained in housing 37, which also contains at least some components of analyte sensing system. A signal can be sent through communication link 48 to a processor (e.g., such as the processor 70 previously described, but with added functionality or an entirely different digital processor). However, the present invention also contemplates that the flow sensing elements, such as the pressure sensor(s) and processor can be contained in housing 37. In which case, ports 234a and 234b would be coupled directly to the housing. In the embodiment illustrated in FIG. 6, the flow element is provided on one side of the gas measurement site. The present invention also contemplates using the gas measurement site to create the pressure drop. In which case, ports 234a and 234b would be provided on either side of the gas measurement cite. Such a configuration is taught, for example, in the '660 patent, the '389 patent, and the '451 application.

In certain embodiments, a mainstream oxygen sensing system is provided that takes into account the effect of the change in temperature and humidity of expired gases in comparison with temperature and humidity of inspired gas (due to the inspired gas not being exposed to body temperature and saturated conditions). This change in temperature and humidity results in measured increases in volume of the exhaled gas and can be accounted for by correcting the inspired oxygen fraction measured. Correction of the inspired oxygen fraction in this manner can result in improved accuracy of oxygen consumption measurement using the Haldane transform. Systems and methods for achieving such improvements in accuracy are described in U.S. patent application Ser. No. 11/948,080, the entire contents of which is hereby incorporated herein by reference.

Figure 7:
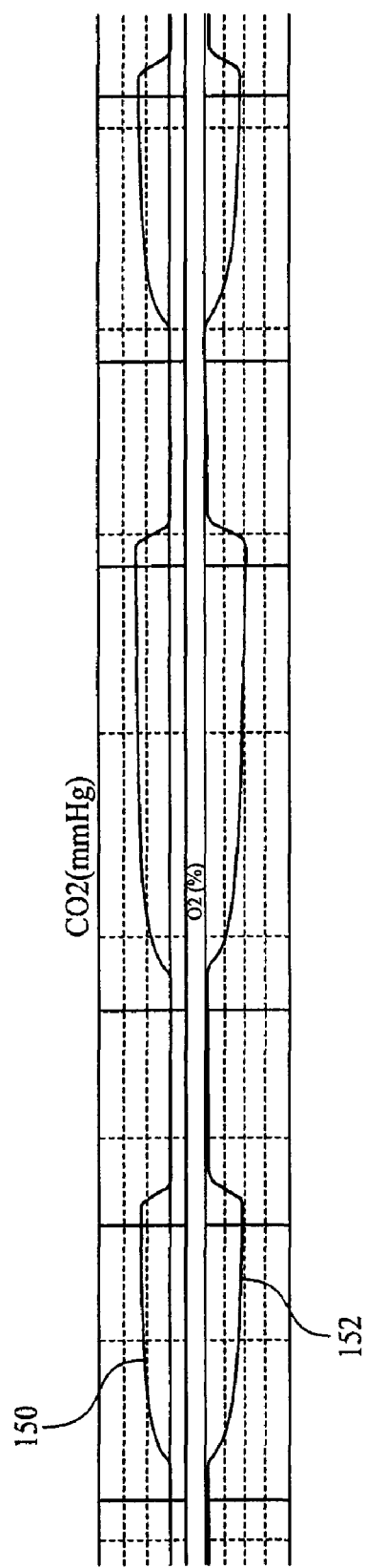
FIG. 7 is a chart showing waveforms representing the relationship between $CO_2$ and $O_2$ concentrations in respiratory gases.

The chart of FIG. 7 depicts waveforms representing concentrations of measured $O_2$ 152 and $CO_2$ 150 in inspiratory and expiratory gases. During respiration, fluctuations observed in the concentration of oxygen closely track those of the concentration of carbon dioxide, except that the form of the $O_2$ waveform 152 is substantially the inverse of the $CO_2$ waveform 150 during an observed time interval. Consequently, the time varying oxygen concentration in the inspiratory and expiratory gases can be approximated using an inverted and appropriately scaled form of the $CO_2$ time varying concentration. It will be appreciated that gas concentrations may be expressed in partial pressures of gas, percentages of gas, in parts per volume of gas, in parts per mass of gas or in any system of measurement conducive to comparing gas concentrations and computing relationships between different gasses as described in this application.

Figure 8:
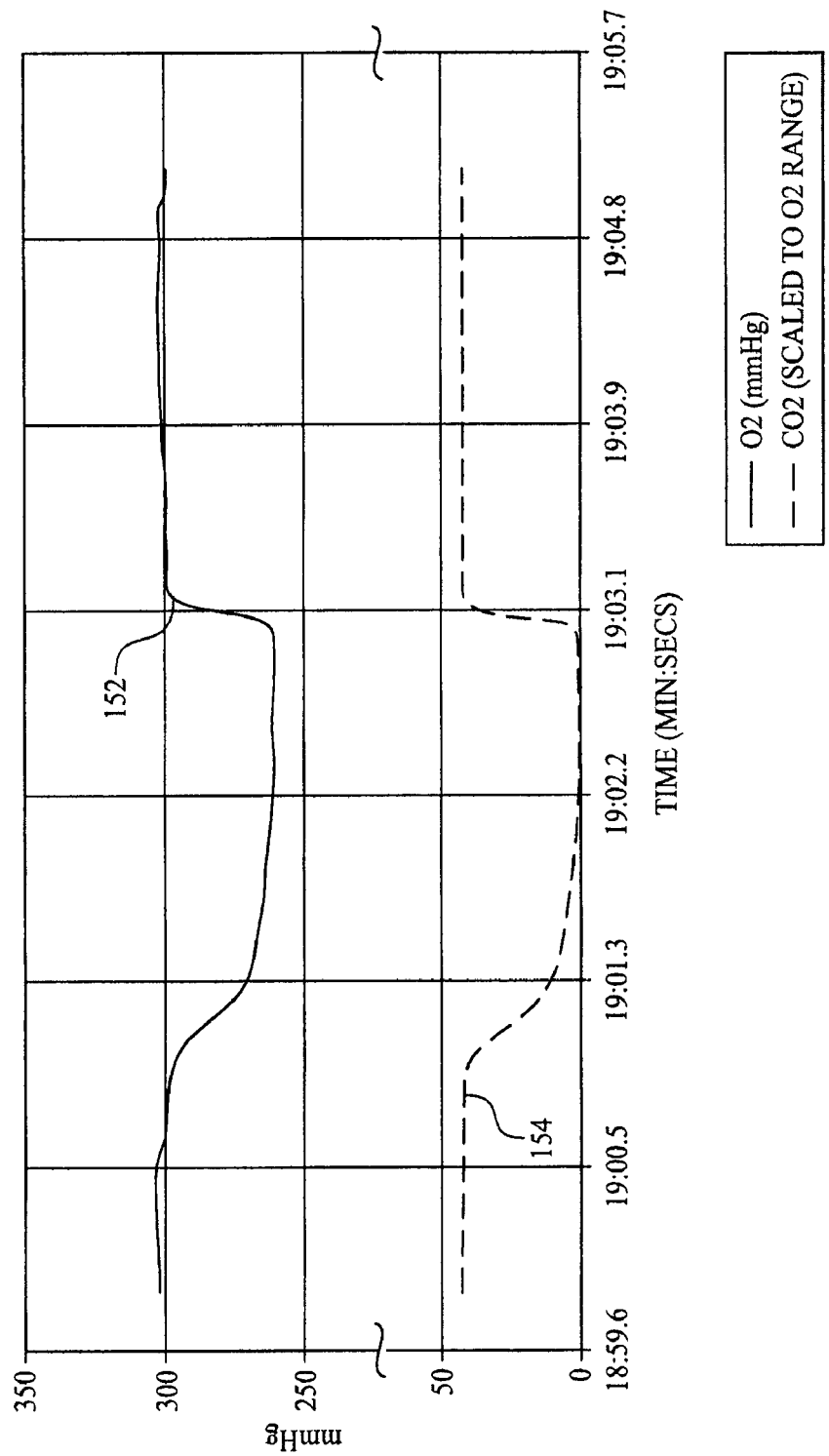
FIG. 8 is a chart showing waveforms representing the relationship between $CO_2$ and $O_2$ concentrations in respiratory gases wherein the $CO_2$ waveform is scaled and inverted.

The chart of FIG. 7 depicts the relationship of waveforms representing concentrations of measured $O_2$ 152 and $CO_2$ 150 when $CO_2$ waveform 150 is inverted and appropriately scaled. Concentration of oxygen may be measured using an oxygen sensor having sufficient accuracy, precision, and measurement speed to correctly measure both a peak (highest level) and a valley (lowest level) of oxygen in the respiratory cycle. These oxygen peak and valley levels can be used to create a scaled reference $O_2$ waveform 154 from the $CO_2$ waveform 150. The scaled reference $O_2$ waveform 154 (FIG. 8) is provided by inverting $CO_2$ waveform 150 and applying a scaling factor calculated as the ratio of measured peak-to-valley level of oxygen to measured peak-to-valley level of $CO_2$.

The shape, form, timing, and spectral content of reference waveform 154 can then be compared to the waveform 152 produced by the oxygen sensor. Certain embodiments employ a curve fitting algorithm or other suitable technique for determining the correlation of signals to measure the quality of the $O_2$ waveform 152. The quality may be quantified using a calculated measure of fit of the $O_2$ waveform 152 to the scaled reference $O_2$ waveform 154. The measurement of quality may be expressed as a time dependent calculated index or other measure of fit.

For example, a least squares fit approach can be used, wherein $R^2$ is a descriptive measure that can vary between 0 and 1 and can be considered to be the relative predictive power of a model. FIG. 11 illustrates this $R^2$ measure, using a portion of the respiration shown in the flow charts of FIGS. 10A and 10B. If the $R^2$ value is below a predetermined or specified value, then the relevant portion of the $O_2$ waveform may be considered to be a candidate for adjustment or replacement. As a non-limiting example, if the $R^2$ value is less than 0.95, portions of the $O_2$ waveform would be a candidate for adjustment or replacement.

It should be appreciated, however, that the quality of the oxygen measurement can be determined or evaluated using many different methodologies or algorithms, and the least squares fit method is but just one example.

It will be appreciated that the concentration of inspired $CO_2$ is typically very low (close to zero). Consequently, in certain embodiments, the inspired concentration of $CO_2$ may be approximated to zero without a significant loss of accuracy in obtaining a scaled reference $O_2$ waveform 154. Such approximation may facilitate ease of computations in obtaining and processing the reference $O_2$ waveform 154.

Embodiments of the present invention take advantage of highly integrated digital signal processing (DSP) technology to perform many of the complex electronic interface functions within a small single chip processor that includes program and data storage as well as analog to digital conversion. Curve fitting algorithms are typically selected based on factors that include processor 70 capabilities, spectral content of the measured waveforms and responsiveness to variations in output. In many embodiments, one or more filters may be implemented to process measured waveforms 150 and 152 and reference waveform 154 at various points in processing, including prior to, during and after curve fitting or other type processing. Filters may be used to remove transients and may be used to eliminate or accommodate slow changes in sensor sensitivity and accuracy that can be attributed to environmental and other factors. Thus, it will be appreciated, combinations of low-pass, high-pass and band-pass filtering may be used to prepare measured and derive signals for processing.

In certain embodiments, reference signal 154 can be used to adjust or replace portions of the measured $O_2$ waveform 152. For example, when oxygen signal quality decreases below a certain threshold, processing logic may indicate that an $O_2$ signal should be amplified or attenuated by a calculated factor. The calculated factor will typically reflect the degree of variation of measured $O_2$ waveform 152 from reference waveform 154. In certain embodiments, application of the calculated factor may be delayed. In such embodiments, the delay may result from the use of filters that remove high frequency components of the measured and derived signals. The delay may also arise because processing logic may delay adjusting the measured $O_2$ signal based on configuration and programmed system parameters. For example, the processing logic may be configured to delay changing the calculated factor by a minimum time period and may be further configured to delay changing the calculated factor by a time period related to the calculated quality of the measured $O_2$ waveform 152. Thus, the processing logic may respond more quickly to large drops in quality than smaller drops in quality. In one example, the predetermined minimum delay can be set to reduce the impact of transients. In another example, the predetermined minimum delay may be modified based on a quantification of instantaneous difference between the measured $O_2$ waveform 152 and the reference $O_2$ waveform 154.

In certain embodiments, the measured $O_2$ signal may be replaced by a reference $O_2$ signal. Typically, processing logic determines that substitution of the reference $O_2$ signal for the measured $O_2$ signal is indicated after determining that the quality of measured $O_2$ waveform 152 has deteriorated below the predetermined threshold level. In certain embodiments, when the quality of measured $O_2$ waveform 152 improves, processing logic may terminate signal substitution. Processing logic may delay substitution and termination of substitution to ensure that deterioration and improvement of quality is not merely transitory.

In certain embodiments, processing logic may determine that the quality of measured $O_2$ waveform 152 varies in a periodic manner. For example, for significant portions of respiration, quality of measured $O_2$ waveform 152 may be consistently below a threshold level. In such circumstances, processing logic may repetitively suppress the measured $O_2$ waveform 152 during respiration and substitute the reference $O_2$ signal in its stead. It will be appreciated that reference $O_2$ signal may be used as a surrogate for all or any portion of the oxygen waveform that has been determined to be of marginal quality.

Typically, the reference $O_2$ signal is generated by processing a measured $CO_2$ signal based on known or calculated relationships between oxygen and carbon dioxide content in inspiratory and expiratory gases. The present invention also contemplates that other combinations of gases can be used to determine quality of a measured gas waveform. For example, the presence of anesthetic gases may be measured and related to the content of oxygen in the inspiratory and expiratory gases.

Figure 9:
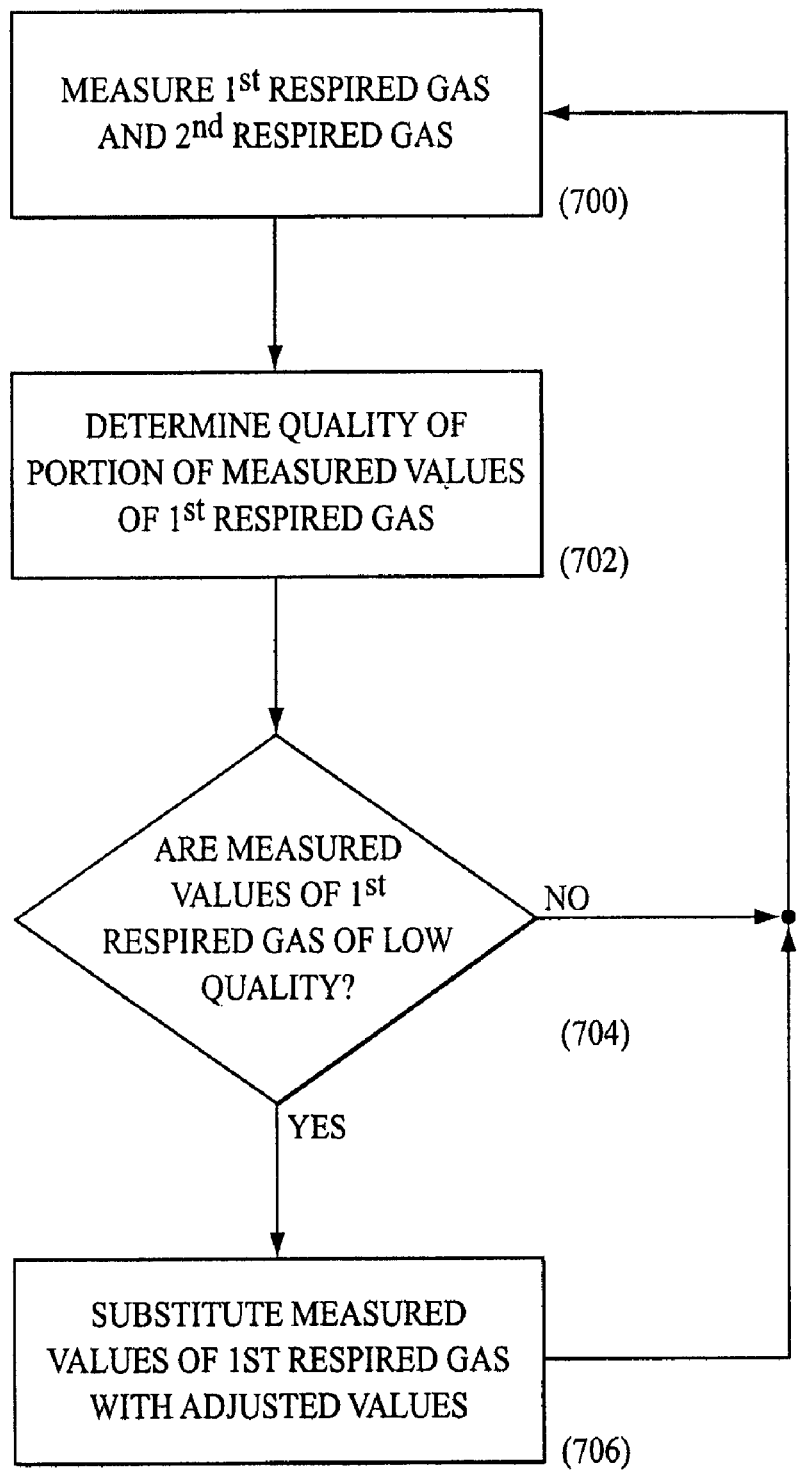
FIG. 9 is a flowchart of a process for monitoring quality of a sensor according to aspects of the present invention.

The flowchart of FIG. 9 depicts a process for controlling substitution of one or more portions of a reference gas content signal for a measured gas content signal based on calculated quality of at least one measured gas content signal. For ease of understanding, the examples of FIGS. 7 and 8 will be referenced in relation to the flowchart. At step 700, the gas content levels of a first respired gas (e.g. $O_2$) and second respired gas (e.g. $CO_2$) are measured, for example, by using the embodiment of FIG. 6. However, other gas content measurement techniques may be used. The levels are typically provided as a signal to processor 70, which determines the quality of the measured $O_2$ waveform 152. It should be noted that the term "respired" is used to describe the gas because the gas in the present invention is delivered to and received from a breathing mammal. However, the present invention contemplates that gas flows other than respired gas are contemplated by the present invention.

As described above, the quality of measured $O_2$ waveform 152 may be determined at step 702 using signal analysis techniques, such as (for example) curve fitting techniques, to obtain a measure of correlation between measured $O_2$ waveform 152 and an inverted, scaled version of measured $CO_2$ waveform 150. At step 704, it is determined whether the quality of measured $O_2$ waveform 152 exceeds a predetermined threshold value. If the quality of measured $O_2$ waveform 152 exceeds the predetermined threshold, then measured $O_2$ waveform 152 may be used for additional calculations, such as to derive oxygen consumption or metabolic estimations based on the quantities of oxygen detected by the $O_2$ sensor. If, however, the quality of measured $O_2$ waveform 152 is of insufficient quality, then portions or all of reference $O_2$ waveform 154 may be substituted for measured $O_2$ waveform 152 at step 706.

While, in one embodiment, the $O_2$ waveform is adjusted by being entirely replaced by the reference $O_2$ waveform, it is contemplated that other types of adjustment are possible, such as application of a corrective factor to the measured $O_2$ waveform 152. The corrective factor may be derived as a function of the measured $CO_2$.

Figure 10A:
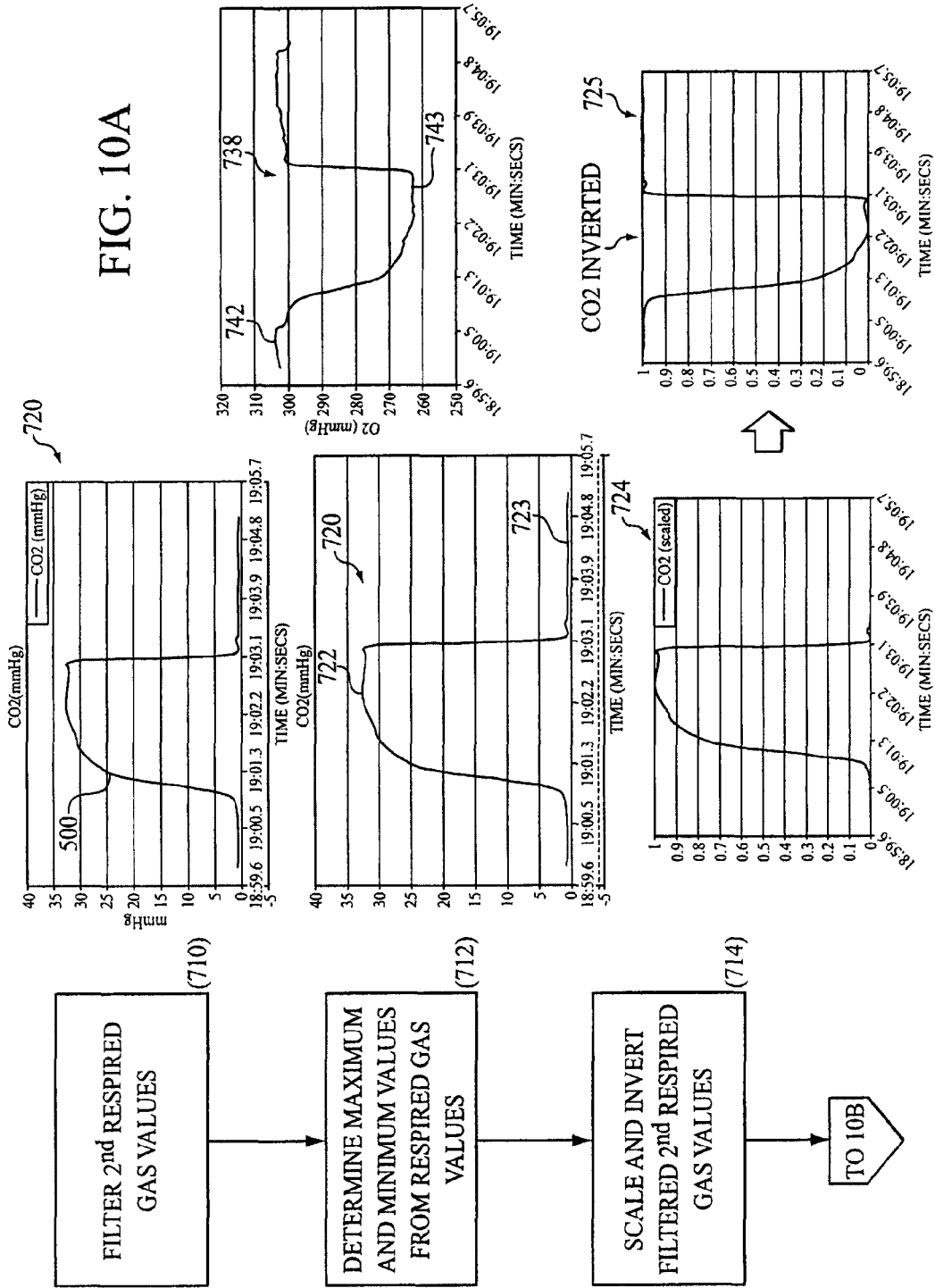
FIGS. 10A-10B provide a flowchart of a process for correcting a signal produced by a sensor according to aspects of the present invention.
Figure 10B:
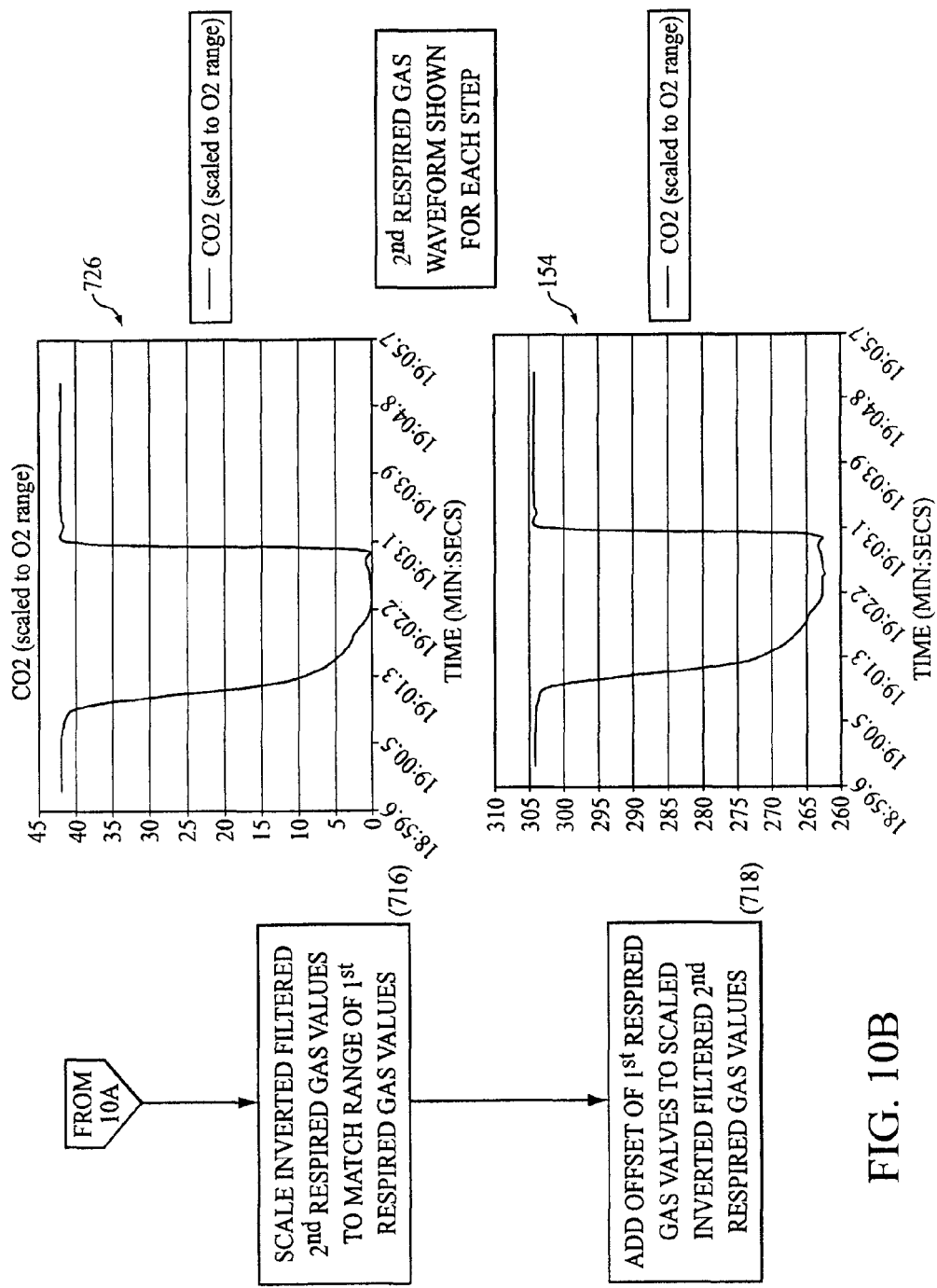
Figure 11:
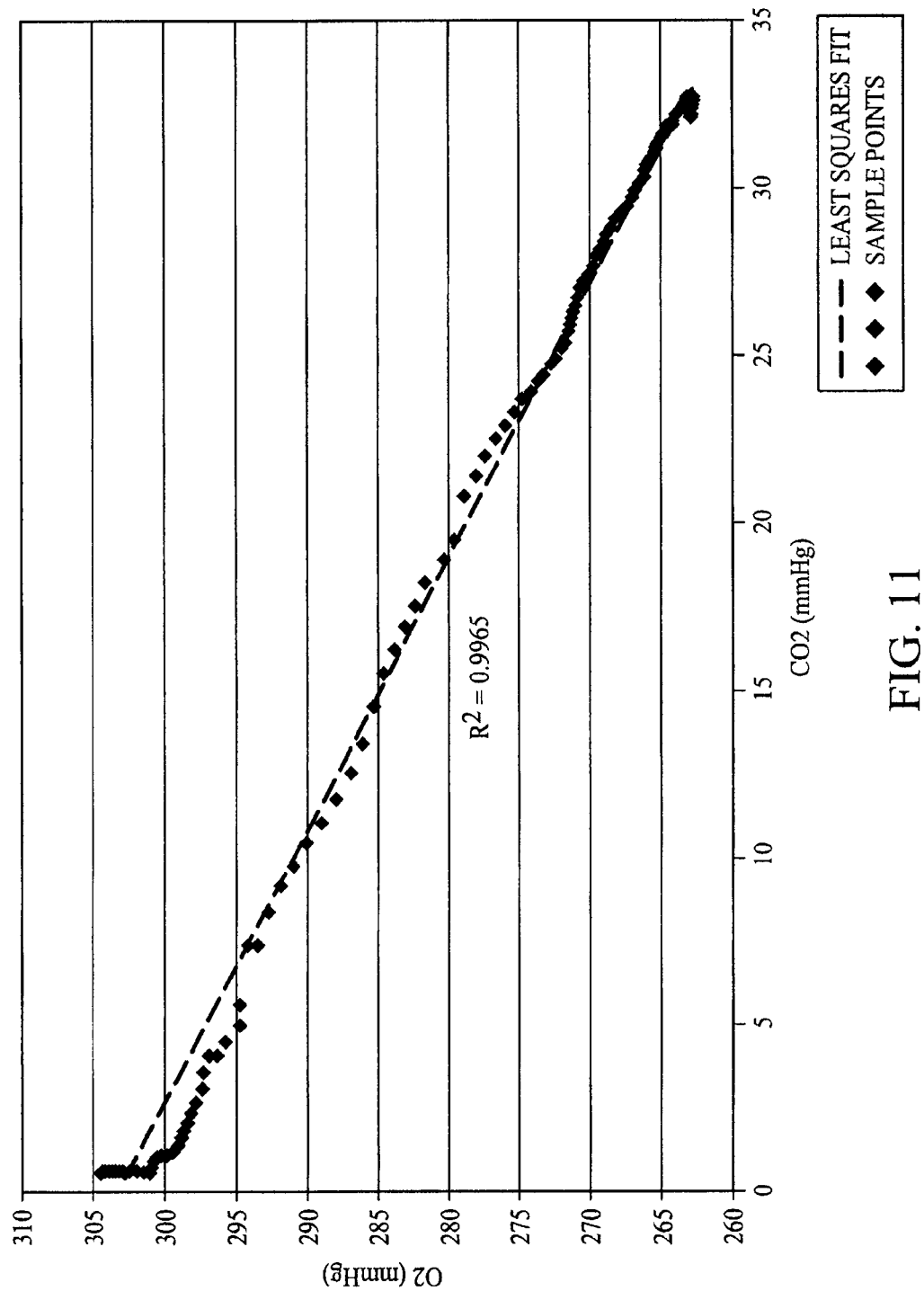
FIG. 11 is a least squares fit plot showing the quality of an oxygen measurement in one example.

The flowchart of FIGS. 10A and 10B describes an exemplary process for generating a reference waveform according to one embodiment of the present invention. For ease of understanding, the examples of FIGS. 7 and 8 will be referenced in relation to the flowchart. At step 710, a waveform 500 of a second respired gas (e.g. $CO_2$) is typically filtered to remove high frequency noise. Typically, waveform 500 is low pass filtered, however, in some embodiments it may be desirable to selectively remove low frequency interference in addition to high frequency noise. Upon filtering, a filtered $CO_2$ waveform 720 is obtained.

In one embodiment, the purpose of filtering the $CO_2$ waveform is so that it is phase and/or frequency matched with the oxygen waveform, such as when the oxygen waveform is the slower of the two (which would be the case when an infrared $CO_2$ sensor and a luminescence quenching oxygen sensor is used). However, in embodiments where the $CO_2$ waveform may be slower than the oxygen waveform, the oxygen waveform may be filtered and/or delayed.

At step 712, a maximum value 722 and a minimum value 723 of filtered $CO_2$ waveform 720 are determined, and a maximum value 742 and a minimum value 743 of the oxygen waveform 738 are determined. For the exemplary $CO_2$ and $O_2$ waveforms shown at step 712 in FIG. 10A, the minimum and maximum values, as well as their difference (range) is shown in the table below:

|  | $CO_2$ (mmHg) | $O_2$ (mmHg) |
| --- | --- | --- |
| min | 0.4 | 262.6 |
| max | 32.8 | 304.55 |
| range | 32.4 | 41.95 |

The difference between maximum and minimum values 742, 743 of the first gas (e.g., oxygen) and the difference between maximum and minimum values 722, 723 of the second gas (e.g., $CO_2$) can then be used at step 714 to compute a scaling value representative of the ratio of the differences in maxima and minima of the waveforms of the first and second gases. For the example above, the scaling value would be 41.95/32.4 or 1.295. This scaling value may then be used at step 714 to obtain a scaled $CO_2$ waveform 724 from the filtered $CO_2$ waveform 720. The scaled $CO_2$ waveform 724 is then inverted to obtain an inverted filtered $CO_2$ waveform 725.

At step 716, additional processing may be performed to condition and adjust inverted filtered $CO_2$ waveform 725. For example, additional scaling of inverted filtered $CO_2$ waveform 725 may be performed to better match certain values of measured $O_2$ waveform 152. At step 718, an offset may be added to the adjusted inverted filtered $CO_2$ waveform 725, thereby generating a reference $O_2$ waveform 154.

Certain embodiments of the present invention provide methods of appraising the measurement accuracy of an oxygen sensor used in conjunction with a carbon dioxide sensor to obtain respiratory assessments of oxygen consumption or other metabolic parameters. As described above, accuracy of the oxygen sensor can be determined by comparing reference $O_2$ waveform 154 with measured $O_2$ waveform 152. Based on the comparison, scaling value adjustments can be obtained and used for calibration of the oxygen sensor. Furthermore, a history of measured $O_2$ waveform 152 samples can be maintained together with histories calibration and waveform quality information. This historical information can be used to adjust an output of the sensor, thereby enhancing accuracy of oxygen measurements obtained from the oxygen sensor.

In certain embodiments, sensitivity of a gas sensor can be calculated under various conditions. For example, sensitivity may be somewhat dependent on instantaneous levels of certain gases present at the sensor and calibration information can be maintained to adjust sensor output signals based on detected levels of gas. Typically, calibration information is associated with combinations of measure instantaneous gas levels and can also include other environmental information available to a processor 70 including, for example, temperatures of sensor, temperature of gases, and so on.

In certain embodiments, oxygen signal quality can be measured by continuously measuring the correlation between the oxygen data stream and the inverted carbon dioxide data stream. Correlation can also be measured using only a portion of the respiratory cycle such as the inspiratory phase only, or the expiratory phase only. Correlation factors obtained at different phases of the respiratory cycle can be combined to obtain a more refined characterization of signal quality.

In certain embodiments, a scaled reference oxygen waveform derived from the $CO_2$ waveform can be used as a surrogate for the oxygen measurement stream for a portion of the respiratory cycle, such as the inspiration phase only or the expiratory phase only, or for the entire cycle. In one example, scaled reference oxygen waveforms derived from the $CO_2$ waveform can be used as a surrogate for the oxygen measurement stream during the transitions between the respiratory phases in order to effectively speed up the response of the oxygen sensor to match that of the $CO_2$ sensor.

The present invention is not limited to quality control of oxygen, but can be applied to other gases that have a known or predictable relationship. For example, in one embodiment, the $CO_2$ waveform can be adjusted based upon the oxygen waveform.

These and other aspects of the present invention yield significant advantages over conventional sensor technology. For example, a reasonably priced, easy to use, self-calibrating oxygen sensor can be provided that exhibits greater speed and accuracy than currently available sensors.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for measuring respiratory gases, comprising:
a first sensor for generating a first signal as a measure of an amount of a first gas;
a second sensor for generating a second signal as a measure an amount of a second gas; and
a processor operatively connected with the first gas sensor and the second gas sensor for
receiving the first and second signals;
calculating a measure of quality of the first signal based on a comparison with the second signal;
substituting a portion of a reference signal for the first signal when the measure of quality falls below a predetermined threshold; and
adjusting the measured amount of the first gas based upon the measured amount of the second gas.

2. The system of claim 1, wherein the adjusting is based on one of an inverted representation of the second signal, scaled versions of the first and second signals, and a scaled representation of the second signal.

3. The system of claim 1, wherein the measure of quality is calculated using curve-fitting of the first signal to the second signal.

4. The system of claim 1, wherein the first gas sensor measures at least one of oxygen and carbon dioxide.

5. The system of claim 4, wherein the first gas sensor is a luminescent quenching sensor.

6. The system of claim 1, wherein the first gas sensor measures inspired oxygen and expired oxygen, and the processor outputs a waveform representative of the adjusted measured amount of at least one of the inspired oxygen and the expired oxygen.

7. The system of claim 1, wherein the second gas sensor measures $CO_2$.

8. The system of claim 7, wherein the second gas sensor is an infrared sensor.

9. The system of claim 1, wherein the second gas sensor measures an amount of expired second gas only, and does not measure the amount of inspired second gas.

10. The system of claim 9, wherein the second gas is $CO_2$ and the amount of inspired $CO_2$ is assumed to be zero.

11. The system of claim 1, wherein the second gas sensor measures both the amount of expired second gas and the amount of inspired second gas.

12. The system of claim 1, wherein the amount of the first respired gas and the amount of the second respired gas are measured as one of partial pressures of gas, and percentages of gas.

13. The system of claim 1, wherein the reference signal is derived from the second signal.

14. The system of claim 13, wherein the reference signal is a scaled inverted version of the second signal.

15. The system of claim 1, wherein the first signal is scaled to compensate for a change in the measure of quality.

* * * * *